Figure 1:
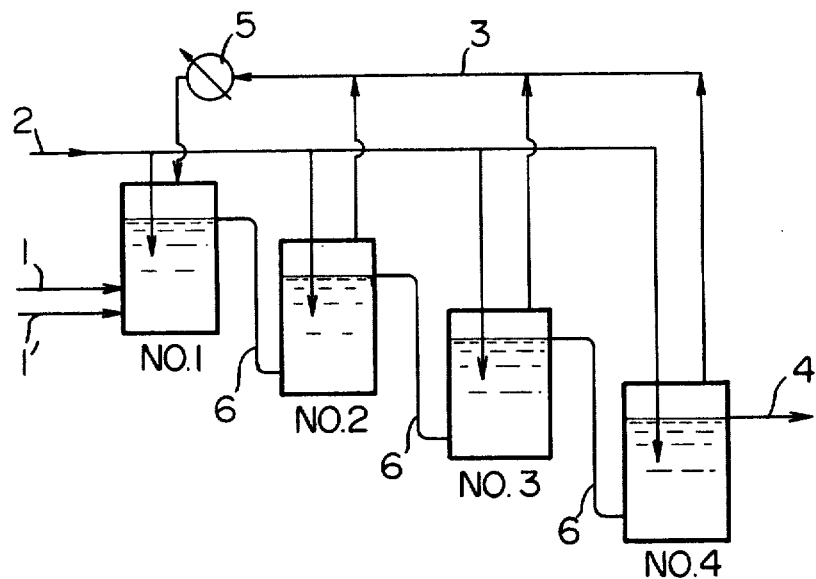

United States Patent [19]

Shima et al.

[11] 3,954,896
[45] May 4, 1976

[54] PROCESS FOR PREPARING MONOALKENYLBENZENES
[75] Inventors: Takeo Shima; Michiyuki Tokashiki; Kazumi Iwata, all of Iwakuni, Japan
[73] Assignee: Teijin Limited, Osaka, Japan
[22] Filed: May 27, 1975
[21] Appl. No.: 581,051

[52] U.S. Cl. .................. 260/668 B; 260/668 F; 260/671 A
[51] Int. Cl.² .......................................... C07C 3/52
[58] Field of Search .......... 260/668 B, 668 R, 668 F

[56] References Cited
UNITED STATES PATENTS

| 3,766,288 | 10/1973 | Shima et al. | 260/668 B |
| 3,865,889 | 2/1975 | Mitchell | 260/668 B |
| 3,904,702 | 9/1975 | Mitchell | 260/668 B |

Primary Examiner—C. Davis
Attorney, Agent, or Firm—J. Edward Hess; Donald R. Johnson

[57] ABSTRACT

In the process for preparing monoalkenylbenzenes by reacting an alkylbenzene and a $C_4 - C_5$ conjugated diene in the presence of an alkali metal catalyst while passing the reactants progressively through a series of successive reaction zones substantially isolated from each other under non-back-flow conditions, the reaction being carried out at this time while feeding said alkylbenzene and alkali metal catalyst to the first reaction zone and the conjugated diene separately to at least two of said zones, and thereafter withdrawing the reaction product from the final reaction zone of said series; the improvement which comprises (1) reacting the reactants including the alkylbenzene, $C_4 - C_5$ conjugated diene and alkali metal catalyst under boiling conditions in at least one of the reaction zone selected from the second and subsequent reaction zones; and (2) recovering the evaporated product from said reaction zone or zones as a liquid and recycling same to a reaction zone preceding that at which the product was evaporated.

4 Claims, 2 Drawing Figures

PROCESS FOR PREPARING MONOALKENYLBENZENES

This invention relates to an improved process by which high purity monoalkenylbenzenes can be prepared at a greatly improved yield and selectivity while advantageously checking the formation of objectionable by-products whose separation from the intended monoalkenylbenzenes is not only complicated but difficult as well.

The monoalkenylbenzenes obtained by reacting an alkylbenzene with a conjugated diene of 4 to 5 carbon atoms, for example, 5-(o-tolyl)pentene-(2) obtained by the reaction of o-xylene with 1,3-butadiene, when cyclized, dehydrogenated and thereafter oxidized, can be converted to naphthalenedicarboxylic acid, which is valuable as the starting material, say, for the preparation of a valuable polyester. Hence, these compounds are commercially valuable.

It is known to prepare alkenylbenzenes by reacting an alkylbenzene with a $C_4 - C_5$ conjugated diene in the presence of an alkali metal catalyst (see, e. g., U.S. Pat. No. 3,244,758). This known process, however, has the shortcoming that a great amount of high molecular weight addition products are formed in addition to the monoalkenylbenzenes in carrying out the reaction, with the consequence that the yield of the intended monoalkynylbenzenes is low. For example, in the alkenylbenzene obtained by reacting o-xylene with 1,3-butadiene in the presence of an alkali metal catalyst there is contained only about 75 – 80 % by weight of monoalkenylbenzenes, i.e., 5-(o-tolyl)pentenes, at most, a major portion of the remainder being compounds resulting from the addition to each mole of o-xylene either 2 or 3 moles of butadiene.

A number of suggestions are known whose object resides in checking the formation of such by-products and improving the selectivity for forming the monoalkenylbenzenes. In one of these suggestions, Belgian Laid Open Specification No. 803,814 (laid open on Feb. 21, 1974) there is disclosed a process wherein the aforesaid reaction of alkylbenzenes and $C_4 - C_5$ conjugated dienes in the presence of an alkali metal catalyst is carried out in a series of successive reaction zones substantially isolated from each other, the reaction being carried out by feeding the alkali metal catalyst to the first reaction zone while feeding the conjugated diene separately to at least two of said reaction zones and thereafter withdrawing the reaction product from the final reaction zone. This reaction, as is well known, is an exothermic reaction, there being evolved, for example, 25 kcal/mol of heat of reaction in the reaction of o-xylene with 1,3-butadiene. Thus, the problem in this case concerned the removal and control this heat of reaction. Hence, there was naturally no mention at all in the foregoing patent of carrying out the reaction under conditions of boiling of the contents of the reaction zone nor of the fact that improvements would be had by carrying out the reaction under such boiling conditions.

A group of inventors, inclusive of a part of the inventors of the present invention, developed a method of removing the foregoing heat of reaction by utilizing the latent heat of vaporization. In the method developed by us, after carrying out the reaction under boiling conditions, the evaporated product is condensed and recycled to the reaction zone at which the reaction was carried out.

In consequence of our further researches into this method of removing the heat of reaction by utilizing the latent heat of vaporization, an amazing fact was found, as shown by the results of the hereinafter given control experiment; i.e., it was found that it was possible to check the formation of by-products to a marked degree and prepare high purity monoalkenylbenzenes in good yield and high selectivity by a procedure comprising carrying out the reaction under boiling conditions in a series of successive reaction zones substantially isolated from each other, the conjugated dienes being fed, as in the aforesaid suggestion, separately to at least two of the reaction zones while, on the other hand, a liquid obtained by condensing the resulting evaporated product is recycled to one of the other reaction zones, with the proviso that the reaction zone to which the condensed liquid is recycled in one which precedes that at which the evaporated product was formed. While the reason for this phenomenon is not yet clear, it was found, as shown by the hereinafter given control experiments, that these marked improvements of the present invention could not be achieved when the evaporated product after being condensed to a liquid is recycled to the same reaction zone at which the reaction was carried out under boiling conditions, or when the condensed liquid is recycled to a zone subsequent to that at which the reaction was carried out.

It is therefore an object of this invention to provide an improved process by which high purity monoalkenylbenzenes can be prepared at a greatly improved yield and selectivity by a simple operation while checking the formation of objectionable by-products.

The foregoing object as well as other objects and advantages of this invention will become apparent from the following description.

According to the invention process for preparing monoalkenylbenzenes comprising carrying out the reaction of an alkylbenzene and a $C_4 - C_5$ conjugated diene in the presence of an alkali metal catalyst while passing the reactants progressively through a series of successive reaction zones substantially isolated from each other under non-back-flow conditions, the reaction being carried out at this time while feeding said alkylbenzene and alkali metal catalyst to the first reaction zone and the conjugated diene separately to at least two of said zones, and thereafter withdrawing the reaction product from the final reaction zone of said series;

1. the reaction of the reactants including the alkylbenzene, $C_4 - C_5$ conjugated diene and alkali metal catalyst is carried out under boiling conditions in at least one of the reaction zones selected from the second and subsequent reaction zones; and 2. the evaporated product from this reaction zone is recovered as a liquid, after which the recovered liquid is recycled to a reaction zone preceding that at which the product was evaporated.

Usable as the aforesaid alkylbenzenes are the compounds having at least one $C_1$ or $C_2$ alkyl radical in attachment to a carbon atom of the benzene ring. As such alkylbenzenes, included are, for example, the compounds of the formula

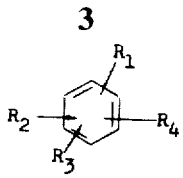

wherein $R_1$ is alkyl radical of 1 or 2 carbon atoms, and $R_2$, $R_3$ and $R_4$, which may be the same or different, are each hydrogen or an alkyl radical of 1 – 3 carbon atoms. Preferred examples of these alkylbenzenes are toluene, xylene, ethylbenzene, trimethylbenzene and tetramethylbenzene. Especially preferred are o-xylene, m-xylene, p-xylene, and the mixtures of two or more of these compounds.

These alkylbenzenes, one of the starting material in the invention process, are preferably used after their dehydration.

The conjugated dienes, the other starting material, are those of 4 – 5 carbon atoms, i.e., 1,3-butadiene and/or isoprene.

The alkali metals, e.g., potassium and sodium are used as the reaction catalyst in the process of this invention. These may be used either singly or in combination of two or more thereof. When using two or more of these metals in conjunction, each may be added to the reaction system singly, as such, or they may be added to the reaction system as an alloy. The conjoint use of metallic potassium and metallic sodium is especially to be preferred. In making conjoint use of the two metals, it is also possible to use that obtained by heat-treating metallic sodium with an inorganic potassium compound, e.g., potassium carbonate, potassium oxide, potassium hydroxide and potassium halides in the absence of oxygen and water. These alkali metal catalysts can also be used supported on such inorganic carriers as, for example, calcium oxide, silica, sodium sulfate, silica-alumina and graphite.

The catalyst is preferably used in proportions per 100 parts by weight of the alkylbenzene present in the reaction system of 0.0005 – 0.1 part by weight of metallic potassium or 0.0005 – 0.05 part by weight of metallic potassium and 0.001 – 0.1 part by weight of metallic sodium when the two are conjointly used. More preferably the catalyst is used in proportions per 100 parts by weight of the alkylbenzene present in the reaction system of 0.002 – 0.05 part by weight of metallic potassium or 0.002 – 0.05 part by weight of metallic potassium and 0.005 – 0.05 part by weight of metallic sodium when the two are conjointly used.

The alkenylation reaction of the aforesaid alkylbenzenes and the aforesaid conjugated dienes can be carried out by, say, a procedure consisting of dispersing the alkali metal catalyst in the liquid alkylbenzene in a finely divided state and thereafter introducing the conjugated diene in a gaseous or liquid state to the reaction zone held at a temperature of about 90°C to about 220°C., and preferably about 100° to about 190°C.

The reaction of the invention process is carried out in a series of successive reaction zones consisting of at least two, and preferably 3 – 15, and more preferably 4 – 8 reaction zones substantially isolated from each other. In carrying out the reaction, the alkylbenzene and the alkali metal catalyst are fed to the first reaction zone, while the conjugated diene is fed separately to at least two reaction zones. Further, in carrying out the reaction by passing the contents of the several reaction zones progressively to the following reaction zones starting from the first reaction zone to the final reaction zone of said series, the reaction is carried out by passing the contents through the reaction zones under such conditions that a part of all of the contents do not return to preceding (upstream) reaction zones, i.e. under non-back-flow conditions. The reaction product is then withdrawn from the final reaction zone of said series.

In the invention process the reaction of the contents including the alkylbenzene, $C_4$ – $C_5$ conjugated diene and alkali metal catalyst must be carried out under boiling conditions in at least one of either the second or subsequent (downstream) reaction zones, and the evaporated product from said reaction zone or zones, after being recovered as a liquid, must be recycled to a reaction zone preceding the reaction zone at which the evaporated product was obtained under boiling conditions.

Figure 2:
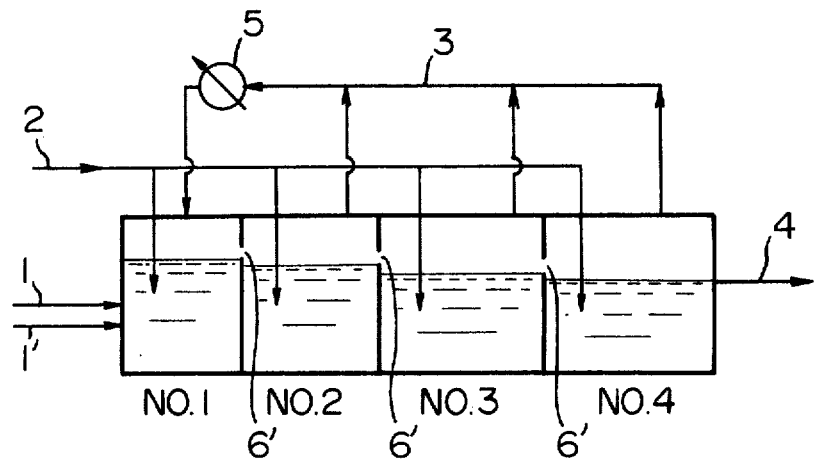

For facilitating its understanding, the invention process will be more fully described hereinafter by reference to the accompanying drawings, in which FIG. 1 is a flow sheet diagram illustrating one mode of practicing the invention process; and FIG. 2 is a similar diagram illustrating another mode of its practice.

FIGS. 1 and 2 illustrate instances of carrying out the reaction in series of successive reaction zones consisting of four successive reaction zones substantially isolated from each other. In the mode shown in FIG. 1, the alkylbenzene is fed to reaction zone No. 1 via line 1, while the alkali metal catalyst is fed to the same reaction zone via line 1'. The alkylbenzene and the alkali metal catalyst need not be fed separately but can be fed together, say, as a dispersion of the alkali metal catalyst in alkylbenzene. In such a case, it is preferred that the feed of the alkylbenzene and the alkali metal catalyst be carried out after having first dispersed the alkali metal catalyst in the alkylbenzene in a dispersion preparing zone equipped with stirring means. In this mode the $C_4$ – $C_5$ conjugated diene is separately fed via line 2 to all of the reaction zones Nos. 1 – 4, but the conjugated diene need not be fed to all of the reaction zones and can be fed to at least two of the reaction zones that have been freely chosen. Further, in this mode the reaction of the contents including the alkylbenzene, $C_4$ – $C_5$ conjugated diene and alkali metal catalyst is carried out under boiling conditions in a total of three reaction zones, i.e. reaction zone No. 2 and subsequent zones, following which the evaporated products obtained from several zones under boiling conditions are collected in line 3 and, after being cooled and recovered as a liquid at a suitable condensing means, say, a heat-exchanging type cooler 5, recycled in toto to reaction zone No. 1, which is a reaction zone preceding that at which the products were evaporated. While the evaporated product consists predominantly of alkylbenzenes whose boiling point is the lowest, there is usually contained a small amount of the conjugate diene in view of the vapor phase equilibrium relationship under boiling conditions. The reaction under boiling conditions need not be carried out at all of the zones including the second and the following zones but need only be carried out at the second and at least one of the reaction zones that follow. Further, the zone to which the evaporated product is recycled as a liquid need not necessarily be the first reaction zone but may be any of the zones that precede that at which the evaporated product was formed. Again, the evaporated product recovered as a liquid need not be recycled in toto but may be only a part thereof. The reaction product is withdrawn from the final reaction zone No. 4 via line 4.

In the mode shown in FIG. 1 the contents of the four reaction zones are caused to flow under non-back-flow conditions progressively from reaction zones Nos. 1 to 4 via lines 6, 6 . . . by the overflow method. Other optional methods in addition to the overflow method which make possible the flow of the contents under non-back-flow conditions can be employed; for example, it is possible to design the system such that pumps are provided in each of the lines between the plurality of reaction tanks to forcibly cause the contents to pass progressively through the successive tanks via lines equipped preferably with check valves. Further, the method to be used in condensing and recovering as a liquid the evaporated product obtained from the reaction zones under boiling conditions can be suitably chosen. Utilizable are either the heat-exchanging type or other types of optional coolers or condenser. Alternately, the evaporated product can be recovered as a liquid by causing it to be absorbed by a suitable absorbing solvent, e.g., the starting alkylbenzene used in the reaction. The liquid recovered in this manner is then recycled to a reaction zone that is on the upstream side with respect to the flow of the contents. For example, in the case of a five-zone reaction system, the vapor evaporated from the second of these zones from the upstream side, after condensation and recovery, is recycled to the first reaction zone. Similarly, the liquid recovered from the third reaction zone can be recycled to either the first or second reaction zone or both. In exactly the same manner, the liquid recovered from the reaction zones at the downstream side can be recycled to an optional zone or zones at the upstream side.

In the invention process the effects of the invention are greater in proportion as the amount of the recycle liquid, i.e., the evaporated product obtained as a liquid, is greater. Again, there is also the tendency that the effects are greater as the point to which the recycling is made is more upstream relative to the flow of the reaction liquid. For these reasons, it is preferred that the foregoing recovered liquid be recycled in toto to reaction zone No. 1. It is also possible to carry out this recycling of the recovered liquid after mixing with the conjugated diene.

FIG. 2 illustrates another mode of practicing the invention process. In this mode the four reaction zones Nos. 1 – 4, which constitute the series of successive reactinn zones substantially isolated from each other, are formed by partitioning a single reaction tank with three partitions having overflow openings 6', but otherwise the setup is identical to that shown in FIG. 1.

In FIGS. 1 and 2 the agitating means usually provided in the several reaction zones have been omitted for simplification of the drawings.

When no separate means for removing the reaction heat from the reaction system or for applying thereto heat other than the reaction heat is provided in practicing the invention process, the evaporated product obtained from the reaction zone under boiling conditions is obtained in an amount substantially corresponding to the latent heat of vaporization equal to the heat of reaction. When a part of the heat of reaction is removed by a method other than boiling, the effects of the present invention decline. On the other hand, when heat other than the heat of reaction is applied to the reaction system (for example, by heating the reaction liquid with a heat exchanger), and the amount evaporated is increased, the effects of the present invention tend to be enhanced. The vaporization pressure about equals the reaction pressure, and it is possible to employ either reduced pressure, atmospheric pressure or superatmospheric pressure conditions. As the reaction is carried out under boiling conditions, the relationship between the pressure and temperature is determined unconditionally. For example, in the case of the reaction of o-xylene and 1,3-butadiene, when normal atmospheric pressure is used as the operating pressure, the reaction temperature becomes 144° – 155°C. The reason for this range of temperature when the reaction pressure is a given value is because the boiling temperature varies in accordance with the concentration of the alkylbenzene. In the usual reaction, boiling takes place in all of the reaction zones when an attempt is made to maintain the reaction temperature constant, but in the invention process it is not necessarily required to cause boiling to take place in all of the reaction zones.

In practicing the invention process, the $C_4 - C_5$ conjugated diene to be fed separately to at least two of the reaction zones need not be fed in equally divided portions, but it is the usual practice to feed the diene in about equally divided portions. The total amount of the $C_4 - C_5$ conjugated diene fed and the amount of the alkylbenzene fed to reaction zone No. 1 are preferably fed in a molar ratio of 1:about 2 – 1 to 1:about 100, more preferably 1:4 – 1:80, and particularly preferably 1:6 – 1:50.

After completion of the reaction, the catalyst used may be separated from the reaction product liquid by such known methods as centrifugal precipitation and gravitational precipitation, or by the separation of the solid phase from the liquid-solid phase at a lower temperature, for example, by such methods as filtration and centrifugation. The separated and recovered catalyst can be recycled to the reaction system and be re-used. Further, the unreacted alkylbenzene and the intended monoalkenylbenzene can be isolated and collected by such methods as, say, distillation from the reaction liquid from which the catalyst has been separated. The isolated and collected unreacted alkylbenzene can be reused as the reaction starting material.

The intended product of the process of this invention, for example, 5-(o-tolyl)pentane, is a useful compound that can be transformed, as hereinbefore mentioned, to naphthalenedicarboxylic acid by submitting the product to a cyclization reaction followed by oxidation. In this case the purity of the monoalkenylbenzene becomes a problem when it is to be cyclized. While the olefinic double bond of the arylalkane, the principal intended product, is as in the case of, say, 5-tolylpentene-(2) at the 2-position, in the case of the conventional methods a considerable amount of isomers whose position of the olefinic double bond differs, such, for example, as 5-tolylpentene-(1), 5-tolylpentene-(3) and 5-tolylpentene-(4) are formed as by-products and become admixed in the reaction product. Of these, that in which the olefinic double bond is in the 1-position, for example, 5-tolylpentene-(1), can be cyclized and converted to an alkyltetralin, but in the case of the others there is the disadvantage that they cannot be converted to an alkyltetralin. It is extremely difficult to remove the aforementioned objectionable isomers from monoalkenylbenzene, the intended product of the invention process. For instance, even through a fraction containing the intended products 5-(o-tolyl) pentene-(1) and 5-(o-tolyl)pentene-(2) obtained by crudely distilling the reaction product of o-xylene and 1,3-butadiene is rectified at a reflux ratio of 20 using a rectification column having a number of theoretical plates corresponding to 50 plates, it is practically impossible to isolate the aforementioned objectionable isomers. In contrast, in the case of the reaction product obtained by the invention process, such undesirable by-products which not only are isolated with difficulty but also impair the quality of the product are contained in an extremely small amount. Hence, there is the advantage that the reaction yield of the cyclized product is also extremely high.

The following example will be given for more fully illustrating the present invention. In the following example, the selectivity for the intended product is defined as follows:

$$\text{Selectivity } (\%) = \frac{\text{Yield of intended monoalkenylbenzene (gram)}}{\text{Yield of the reaction product of alkylbenzene and the } C_4 - C_5 \text{ conjugated diene (gram)}} \times 100$$

EXAMPLE 1

The apparatus used in this experiment was a continuous reaction apparatus consisting of five jacketed reaction tanks each having a capacity of 20 liters (effective liquid holding capacity of 12 liters) and equipped with a stirrer, the several tanks being connected in series with overflow type lines, the reaction liquid of tank No. 1 flowing into tank No. 2 via an overflow line and successively through tanks Nos. 3, 4 and 5, from which final tank the reaction product was withdrawn. In this experiment the unreacted o-xylene separated and recovered by distillation from the alkenylation reaction product withdrawn from the fifth tank and dehydrated o-xylene in an amount corresponding to that consumed in the reaction were combined and heated up to 135°C. with a preheater. This was then fed continuously to tank No. 1 at a rate of 19 kg per hour. The temperatures of the tanks Nos. 2 – 5 were adjusted so that boiling at normal atmospheric pressure would take place by heating these tanks via their jackets with heated oil. The evaporated vapors were all brought together and condensed in a condenser, following which the total amount of the liquid was recycled to the first tank via a flow meter. The stirrers of the several tanks were rotated at 200 rpm, and an alloy of weight ratio of metallic sodium to metallic potassium of 1:1 was fed to the first tank at a rate of 10 grams per hour. Four hours after the initiation of the feed of o-xylene and the catalyst, dehydrated 1,3-butadiene was separately introduced continuously to the several tanks Nos. 1 – 5 at a rate of 0.22 kg per tank (a total for the five tanks of 1.10 kg per hour) to carry out the reaction of o-xylene and 1,3-butadiene. As the reaction proceeded, the concentration of the alkenylbenzenes increased, and the boiling point of the liquid contained in the reaction tanks at normal atmospheric pressure started to rise. Hence, the heating of the reaction tanks via the jackets was gradually increased, and the total amount of the condensed recovered liquid recycled to tank No. 1 was adjusted at 6.5 kg/hr. The reaction liquid thus overflowing from tank No. 5 was introduced to a decanter, and the catalyst used in the reaction was separated. The hydrocarbon liquid phase resulting on separation of the catalyst was then continuously distilled at a reduced pressure distillation column to separate the hydrocarbon liquid phase into an unreacted o-xylene fraction and a fraction consisting predominantly of alkenylbenzenes. The recovered unreacted o-xylene fraction was recycled to the aforementioned alkenylation reaction and reused. On the other hand, the fraction consisting predominantly of alkenylbenzenes was submitted to further distillation at reduced pressure to obtain continuously at a rate of 2.79 kg per hour the intended product of 99.8% purity consisting of 5-(o-tolyl)pentene-(1) and 5-(o-tolyl)pentene-(2), the intended monoalkenylbenzenes.

When the alkenylation products contained in the reaction liquid obtained from tank No. 5 was analyzed by gas chromatography and the distillation method after continuously carrying out the foregoing operation for 20 days, the following results were obtained.

| | |
|---|---|
| 5-(o-tolyl)pentene-(1): | 0.44 wt. % |
| 5-(o-tolyl)pentene-(2): | 14.15 wt. % |
| 5-(o-tolyl)pentene-(3): | 0.00 wt. % |
| 5-(o-tolyl)pentene-(4): | 0.03 wt. % |
| By-products of higher boiling points than 5-(o-tolyl)pentenes | 1.05 wt. % |

Of these, the selectivity of the components that could be converted to 1,5-dimethyltetralin by the cyclization reaction was 93.1%.

CONTROL 1

The experiment was carried out by exactly the same procedure as in Example 1, except that the condensers and recycle lines (a total of four sets) were so arranged that the evaporated products evaporated from the several tanks Nos. 2 – 5 could be condensed and recycled to the several reaction tanks at which the evaporated products were formed. The reaction liquid from tank No. 5 was analyzed as follows:

| | |
|---|---|
| 5-(o-tolyl)pentene-(1): | 0.82 wt. % |
| 5-(o-tolyl)pentene-(2): | 12.80 wt. % |
| 5-(o-tolyl)pentene-(3): | 0.06 wt. % |
| 5-(o-tolyl)pentene-(4): | 0.22 wt. % |
| By-products of higher boiling points than 5-(o-tolyl)pentenes | 2.12 wt. % |

As a result, the selectivity in the alkenylation reaction was 85.0%.

CONTROL 2

The experiment was carried out exactly as in Example 1, except that the vapors evaporated from tanks Nos. 2 – 5 were combined and, after condensing at a condenser, recycled in toto to tank No. 5. The alkenylation products contained in the reaction product liquid obtained from tank No. 5 were analyzed with the following results.

| | |
|---|---|
| 5-(o-tolyl)pentene-(1): | 0.77 wt. % |
| 5-(o-tolyl)pentene-(2): | 11.44 wt. % |
| 5-(o-tolyl)pentene-(3): | 0.12 wt. % |
| 5-(o-tolyl)pentene-(4): | 0.58 wt. % |
| By-products of higher boiling points than 5-(o-tolyl)pentenes | 3.10 wt. % |

As a result, the selectivity in the alkenylation reaction was 78.1 %.

We claim:

1. In the process for preparing monoalkenylbenzenes by reacting an alkylbenzene and a $C_4 - C_5$ conjugated diene in the presence of an alkali metal catalyst while passing the reactants progressively through a series of successive reaction zones substantially isolated from each other under non-back-flow conditions, the reaction being carried out at this time while feeding said alkylbenzene and alkali metal catalyst to the first reaction zone and the conjugated diene separately to at least two of said zones, and thereafter withdrawing the reaction product from the final reaction zone of said series; the improvement which comprises 1. reacting the reactants including the alkylbenzene, $C_4 - C_5$ conjugated diene and alkali metal catalyst under boiling conditions in at least one of the reaction zones selected from the second and subsequent reaction zones; and
2. recovering the evaporated product from said reaction zone or zones as a liquid and recycling same to a reaction zone preceding that at which the product was evaporated.

2. The process of claim 1 wherein the reaction of the reactants including the alkylbenzene, $C_4 - C_5$ conjugated diene and alkali metal catalyst is carried out under boiling conditions at the second and all subsequent reaction zones.

3. The process of claim 1 wherein the liquid recovered from the evaporated product obtained from the reaction zones under boiling conditions is recycled in toto to the first reaction zone.

4. The process of claim 1 wherein the molar ratio of the total amount of the conjugated diene separatedly fed to the amount of the alkylbenzene fed to the first reaction zone ranges from 1 : about 2 to 1 : about 100.

* * * * *